US00PP37121P2

(12) United States Plant Patent
Neu

(10) Patent No.: US PP37,121 P2
(45) Date of Patent: Dec. 2, 2025

(54) ***PELARGONIUM* PLANT NAMED 'KLEPZ24880'**

(50) Latin Name: *Pelargonium zonale*
Varietal Denomination: KLEPZ24880

(71) Applicant: KLEMM + SOHN GMBH & CO. KG, Stuttgart (DE)

(72) Inventor: Nina Neu, Weissach im Tal (DE)

(73) Assignee: KLEMM+SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/179,441

(22) Filed: Apr. 15, 2025

(51) Int. Cl.
*A01H 5/02* (2018.01)
*A01H 6/42* (2018.01)

(52) U.S. Cl.
USPC ..... Plt./328

(58) Field of Classification Search
USPC ..... Plt./263.1, 324, 325, 328
See application file for complete search history.

(56) References Cited

U.S. PATENT DOCUMENTS

PP35,942 P2 * 7/2024 Glawe ..... Plt./329

* cited by examiner

*Primary Examiner* — Karen M Redden
(74) *Attorney, Agent, or Firm* — Weatherly IP Solutions, LLC; James M. Weatherly

(57) ABSTRACT

A new *Pelargonium* plant particularly distinguished by cerise, pink flower color and strong zonation, is disclosed.

1 Drawing Sheet

Genus and species: *Pelargonium zonale.*
Variety denomination: 'KLEPZ24880'.

BACKGROUND OF THE NEW PLANT

The present invention comprises a new and distinct variety of *Pelargonium*, botanically known as *Pelargonium zonale* and hereinafter referred to by the variety name 'KLEPZ24880'. 'KLEPZ24880' originated from a controlled cross in July 2019 in Juja, Kenya between the commercial female *Pelargonium* variety 'KLEPZ17484' (U.S. Plant Pat. No. 30,335) and the proprietary male *Pelargonium* variety 'PZ-2017-7370' (unpatented).

Seeds from the controlled cross were obtained. The seeds were sown and plants were grown for evaluation. A single plant was selected in June 2020 and subsequently named 'KLEPZ24880'. In July 2020 'KLEPZ24880' was first vegetatively propagated by vegetative stem cuttings in Stuttgart, Germany. 'KLEPZ24880' was found to reproduce true to type in successive generations of asexual propagation via stem cuttings in Stuttgart, Germany.

SUMMARY

The following are the most outstanding and distinguishing characteristics of this new variety when grown under normal horticultural practices in Stuttgart, Germany.

1. Cerise pink flower color; and
2. Strong zonation.

DESCRIPTION OF THE PHOTOGRAPH

This new *Pelargonium* plant is illustrated by the accompanying photograph which shows an overall view of the plant in a pot. The photograph is of an approximately 14-week-old plant grown indoors in Stuttgart, Germany, in May 2023. The colors shown are as true as can be reasonably obtained by conventional photographic procedures.

DESCRIPTION OF THE NEW VARIETY

The following detailed descriptions set forth the distinctive characteristics of 'KLEPZ24880'. Data was collected on 12-week-old plants in Stuttgart, Germany under greenhouse conditions in March 2025. Color references are to The R.H.S. Colour Chart of The Royal Horticultural Society of London (R.H.S.), 5$^{th}$ edition (2007).

Classification:
- *Family.*—Geraniaceae.
- *Botanical.*—*Pelargonium zonale.*
- *Common.*—*Pelargonium.*
- *Designation.*—'KLEPZ24880'.

Parentage:
- *Female parent.*—'KLEPZ17484' (U.S. Plant Pat. No. 30,335).
- *Male parent.*—'PZ-2017-7370' (unpatented).

Plant:
- *Form.*—Bushy.
- *Habit.*—Mounding.
- *Height (from top of soil).*—16.5 cm.
- *Width (horizontal plant diameter).*—21.5 cm.
- *Natural flowering season.*—March to October.
- *Propagation type.*—Vegetative by stem cuttings.
- *Time to produce a finished flowering plant.*—12 weeks.
- *Time to initiate and develop roots.*—4 weeks.
- *Root description.*—Fine, dense, white, RHS 158A.
- *Flower type.*—Zygomorphic.

Stems:
- *Quantity of stems per plant.*—4 to 7.
- *Color.*—RHS 144A.
- *Surface texture.*—Pubescent.
- *Stem form.*—Round.

*Diameter.*—0.8 cm.
*Length.*—3.0 cm to 6.5 cm.
*Internode length.*—1.2 cm.
*Anthocyanin.*—Present, RHS 200C.

Leaves:
*Arrangement.*—Alternate.
*Shape.*—Reniform.
*Apex.*—Round.
*Base.*—Open.
*Margin.*—Crenate.
*Surface texture both surfaces.*—Pubescent.
*Length.*—6.5 cm.
*Width.*—8.0 cm.
*Color.*—Upper surface: RHS 147A. Lower surface: RHS 147B.
*Zonation.*—Strong zonation, distance to base 1.7 cm, distance to margin 1.3 cm.
*Zonation color.*—RHS 200B.
*Depth of sinus.*—2.4 cm.
*Petiole.*—Length: 5.0 cm. Diameter: 0.2 cm. Color: RHS 144A. Strength: Soft.
*Venation pattern.*—Palmate.
*Venation color.*—Upper surface: RHS 147A. Lower surface: RHS 144A.

Inflorescence:
*Lastingness of flowers on the plant.*—6 to 8 days.
*Umbels.*—Quantity of umbels per plant: 4 to 6. Length: 5.0 cm. Diameter: 9.0 cm.
*Individual florets of the umbel.*—Quantity of florets per umbel: 9 to 11. Depth: 1.7 cm. Diameter: 4.7 cm.
*Fragrance.*—Absent.

Flower buds:
*Cluster shape.*—Round.
*Cluster size.*—Length: 1.2 cm. Width: 1.5 cm.
*Surface texture.*—Pubescent.
*Bud.*—Height: 0.6 cm. Width: 0.5 cm. Shape: Round. Apex: Acute. Base: Obtuse. Margin: Entire. Color: RHS 144A.

Petals:
*Quantity per flower.*—7.
*Shape.*—Spatulate.
*Apex.*—Round.
*Base.*—Obtuse.
*Margin.*—Entire.
Length.—2.6 cm.
Width.—2.4 cm.
*Surface texture.*—Upper surface: Smooth. Lower surface: Smooth.
*Color of lobes.*—Upper lobes: Upper surface: RHS 67A basic color, RHS 45B at base. Lower surface: RHS 45C. Lower lobes: Upper surface: RHS 67A. Lower surface: RHS N66A.
*Markings.*—None just a slight color shift from pink to red at base of upper lobes.

Petaloids:
*Quantity per flower.*—2 to 4.
*Shape.*—Crippled and deformed spatulate.
*Apex.*—Round or obtuse.
*Base.*—Obtuse.
*Margin.*—Entire.
*Length.*—0.5 cm to1.8 cm.
*Width.*—0.2 cm to 1.0 cm.
*Surface texture.*—Upper surface: Smooth. Lower surface: Smooth.
*Color.*—Upper surface: RHS 67A. Lower surface: RHS N66A.

Sepals:
*Number per flower.*—5.
*Shape.*—Elliptic.
*Apex.*—Acute.
*Base.*—Obtuse.
*Margin.*—Entire.
*Surface texture.*—Upper surface: Smooth. Lower surface: Pubescent.
*Color.*—Upper surface: RHS 144A at tip, RHS 46A at base. Lower surface: RHS 144A at tip, RHS 46A at base.
*Length.*—1.2 cm.
*Width.*—0.2 cm.

Pedicel:
*Length.*—3.1 cm.
*Diameter.*—0.2 cm.
*Color.*—RHS 200B.
*Surface texture.*—Pubescent.
*Strength.*—Medium.

Peduncle:
*Length.*—11.0 cm.
*Diameter.*—0.3 cm.
*Color.*—RHS 200D.
*Texture.*—Pubescent.
*Strength.*—Strong.

Reproductive organs:
*Stamens.*—Quantity per flower: 6 to 9. Anther length: 0.2 cm. Filament length: 0.7 cm. Filament color: RHS NN155D at base, RHS 50A at tip. Pollen amount: Many or abundant. Pollen color: RHS 34B.
*Pistils.*—Number: 1. Stigma color: RHS N34A. Style length: 0.2 cm. Style color: RHS N34A. Ovary arrangement: Central. Ovary color: RHS 200B. Ovary diameter: 0.2 cm. Ovary length: 0.4 cm. Ovary Texture: Pubescent.

Fruit and seed set: None observed.
Disease and pest/insect resistance: None observed.

COMPARISON WITH PARENTAL LINES AND KNOWN VARIETY

'KLEPZ24880' is distinguished from its parents as described in Table 1.

TABLE 1

Comparison with Parental Lines

| Characteristic | 'KLEPZ24880' | Female parent | Male parent |
|---|---|---|---|
| Flower color | Cerise pink | Purple red | Magenta pink |
| Leaf zonation | Strong | Very strong | Medium |

'KLEPZ24880' can be compared to the commercial variety PAC Neona (patent status unknown). Differences between the two varieties are described in Table 2:

TABLE 2

Comparison with Similar Variety

| Characteristic | 'KLEPZ24880' | PAC Neona |
|---|---|---|
| Leaf zonation | Strong | Weak |
| Flower color | Cerise pink | Magenta pink |

I claim:

1. A new and distinct variety of *Pelargonium* plant named 'KLEPZ24880' as illustrated and described herein.

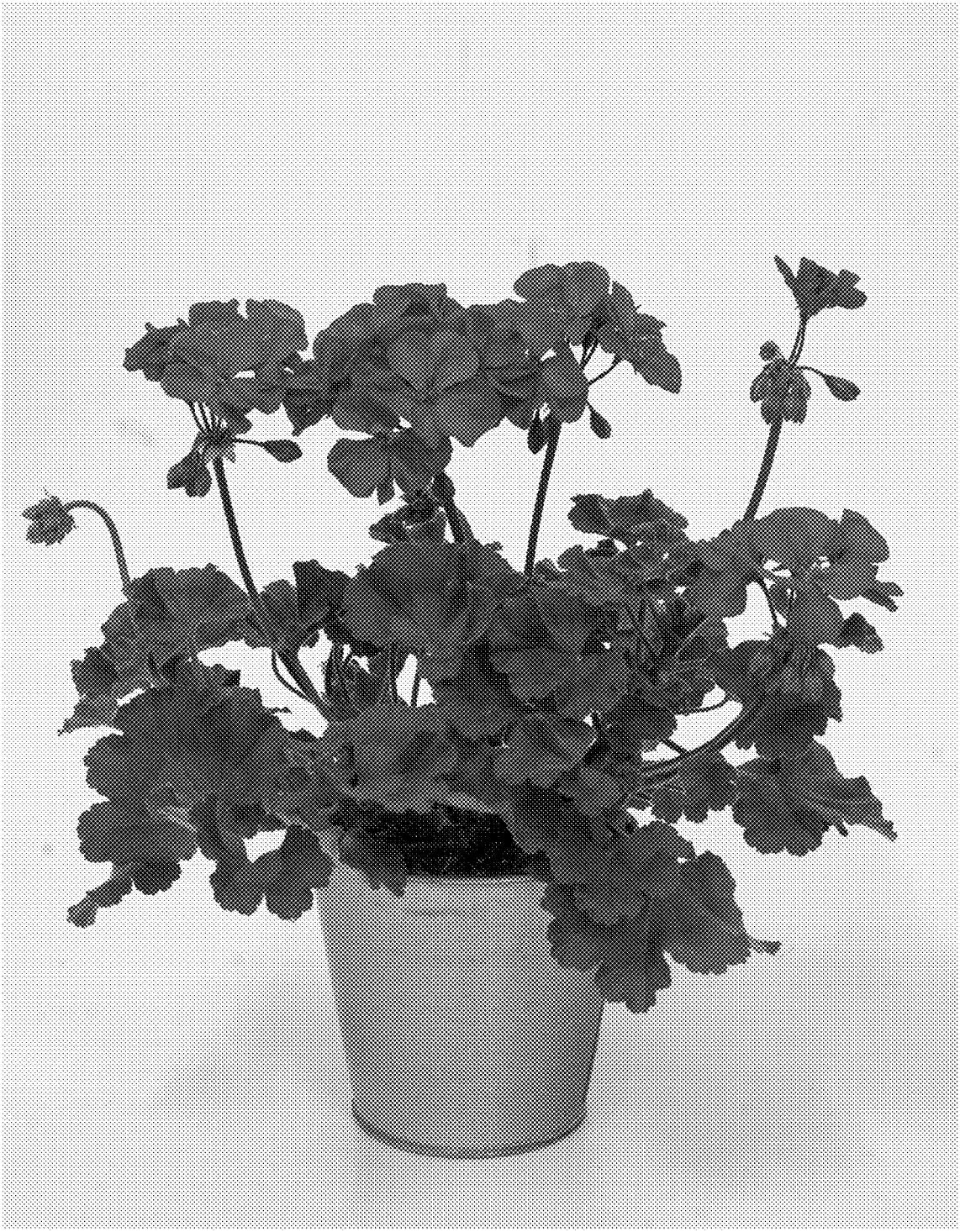

* * * * *